the viscosity of the bisphenol containing solution may be sensed from the first addition of the diacid halide until such addition is terminated. The rate of addition of the diacid halide to the bisphenol containing solution will be high during the initial stages of polymerization and decrease to zero at the solution viscosity limit.

In a preferred embodiment, the polymerization reaction may be carried out in a continuous manner, by which the reactants are continuously introduced into the reaction zone and the polymer product is continuously prepared and withdrawn. This may be achieved, for example by utilizing a cylindrical tube, having static mixers as a reaction vessel. The bisphenol containing solution is passed through the tube while adding the diacid halide at various points along the longitudinal axis in response to the viscosity of the polymer containing solution as it is sensed at the outgoing portion of the tube. Thus, the diacid halide is added in large amounts at the downstream portion of the tube and in gradually decreasing amounts at positions further upstream in the tube.

The final concentration of the polymer in solution is about 3 to about 25%, preferably from about 5 to about 20% and most preferably from about 7 to about 15%. At these percentages of concentration, the solution viscosity will generally vary from about 1 to about 3000 poise, preferably from about 5 to about 200 poise and most preferably from about 10 to about 1000 poise.

Polymerization is effective at temperatures which may vary from about 0 to about 200° C., preferably from about 10 to about 100° C., and most preferably from about 15 to about 150° C., and at pressures which may vary from about .01 to about 10 atmospheres and preferably from about 0.1 to about 10 atmospheres. Agitation of the reactants will be sufficient to evenly disperse the diacid halide throughout the bisphenol containing solution to avoid a build-up of the concentration of the diacid halide in a localized area within the reaction mixture. Such agitation may be supplied by any of the standard means of mixing such as by stirrier, shaker, static mixer, spray nozzle or other flowing agitating systems.

After polymerization the polymer is generally recovered by washing the polymer containing solution with dilute, aqueous hydrogen chloride to neutralize the excess acid acceptor. The polymer solution is then washed with water to remove salts and collected in any suitable manner such as by evaporation of the solvent or by precipitation of the polymer in a suitable non-solvent such as acetone or methanol. The polymer may then be concentrated to a desired spinning dope viscosity or diluted without isolation if the polymer is a solid, and thereafter processed for shaping, e.g., spun or cast for making fibers or films, respectively.

Generally, the solution polymerization technique described herein is utilized to control the molecular weight of the halogenated aromatic polyester in a manner sufficient to obtain a polymer having inherent viscosity (IV) limits which may vary from about 0.4 to about 1.7, preferably from about 0.6 to about 1.5, and most preferably from about 0.7 to about 1.2, which are indicative of polymers having a weight average molecular weight of about 25,000 to about 150,000, preferably from about 41,000 to about 127,000, and most preferably from about 50,000 to about 97,000.

The above described inherent viscosity ranges will generally correspond to solution viscosity limits of about 1 to about 3000 poise, typically from about 5 to about 1000 poise and preferably from about 30 to about 95 poise at the typical final solution concentrations described above.

The halogenated aromatic polyesters prepared by the process of the presently claimed invention may be dissolved in a suitable spinning or casting solvent, such as methylene chloride or tetrahydrofuran and formed into a shaped article, such as a fiber or film.

The halogenated aromatic polyesters described herein have been used to produce a number of inherently non-burning fibrous materials which offer the public a great degree of fire safety, particularly when fibrous articles are required for use in fire-control environments, e.g., children's sleepwear, suits for fire fighters, hospital furnishings, and uniforms for military and civilian personnel.

The following examples are given as specific illustrations of the claimed invention. It should be understood, however, that the invention is not limited to the specific details set forth in the examples. All parts and percentages in the examples as well as in the remainder of the specification are by weight unless otherwise specified.

EXAMPLE I

The objective of this example is to obtain a polymer with an inherent viscosity between 0.9 and 1.1 which corresponds to a weight average molecular weight (AW) of from 68,000 to about 87,000 and a solution viscosity limit of from about 40 to about 71 poise. Thus, a brominated aromatic polyester containing bromine chemically bound to an aromatic ring and possessing the structural formula heretofore illustrated where X and Y are bromine groups, R and R' are methyl groups and n is about 100 is prepared by solution polymerization in the following manner.

The amounts of reactants utilized in this example are based on theoretical stoichiometric requirements to achieve the desired molecular weight and no correction is made for other factors such as impurities in the reactants which might affect the theoretical requirements. Thus, 201.7 parts by weight of 4,4' - isopropylidene - 2,2' , 6,6' - tetrabromodiphenol are added to a reaction vessel containing about 1800 parts by weight of methylene chloride and 80 parts by weight of triethylamine under agitation.

A solution of a mixture of diacid halides comprising 44.7 parts by weight of previously distilled isophthaloyl chloride and about 29.8 parts by weight of previously distilled terephthaloyl chloride and 213.8 parts by weight of methylene chloride is then added at a rate of 3.37 liters per minute to the bisphenol containing solution over a period of time of about one half hour. and at a temperature of about 30° C. The viscosity of the resulting solution is then sensed by measuring the viscosity of an in line sample at 30° C with a Brookfield viscometer and found to be less than 2 poise.

An additional amount of the same diacid halide solution which has been diluted to about 2.5 percent by weight is then added at a rate of 0.76 liters per minute. After a period of time of about 20 to 30 minutes the solution viscosity increases to about 2 poise at 30° C. and the flow rate is decreased to 0.26 liters per minute over a period of about 20 to 30 minutes. The viscosity of the solutions is then sensed in the manner described above and found to be 20 poise. The previously diluted diacid halide solution is then charged to the reaction vessel at a flow rate of about 0.11 liters per minute in progressively shorter increments until the solution vis-

LATENT CATALYSTS FOR PROMOTING REACTION OF EPOXIDES WITH PHENOLS AND/OR CARBOXYLIC ACIDS

This is a continuation of application Ser. No. 481,599, filed June 21, 1974, now abandoned.

BACKGROUND OF THE INVENTION

1. Field of the Invention

This invention pertains to novel latent catalysts for promoting reaction between vicinal epoxides and phenols and/or carboxylic acids (or anhydrides of such acids). Such reactions are commercially important in that functional monomers (e.g. hydroxyethyl acrylate), hydraulic fluids (e.g. 2-phenoxyethanol) and high molecular weight linear or cross-linked epoxy resins are thus produced.

2. Description of the Prior Art

The reactions between epoxides and phenols and/or carboxylic acids (or anhydrides) have been extensively studied and many patents have issued which describe these well known classes of reactants. See, for example, U.S. Pat. Nos. 2,216,099, 3,377,406, 3,547,885, 2,633,458, 3,477,990, 3,694,407, 2,658,885, 3,547,881, 3,738,862; Canadian Pat. No. 893,191, German Pat. DT No. 2,206,218, and the text "Handbook of Epoxy Resins" by H. Lee and K. Neville, McGraw Hill, N. Y. (1967).

In addition to describing the classes of reactants, the above patents also show that (1) a catalyst is required to attain a satisfactory reaction rate and (2) those skilled in the art recognize that the reaction between epoxides and phenols is not, mechanistically speaking, the same as the reaction between epoxides and carboxylic acids (or anhydrides) due to the differences in products. The latter point is illustrated by the fact that substantially linear polymers are produced (U.S. Pat. No. 3,477,990) by reacting epoxy resins with polyfunctional phenols in the presence of a catalyst whereas cross-linked polymers are produced (U.S. Pat. No. 3,547,885) by reacting the same epoxy resins with a polycarboxylic acid (or anhydride) in the presence of the same catalysts. The reactive species which catalyzes the reaction is therefore believed to be different in each instance. Thus, compounds which catalyze one reaction would not necessarily be expected to catalyze the other.

Several problems have been encountered in using many of the prior art catalysts. In many instances, the catalysts react with the epoxy reactant and thus preclude the option of marketing a blend comprising an epoxy resin and a catalyst; this blend is commonly referred to as a "precatalyzed epoxy resin". In other instances, the problem associated with the prior art catalysts is selectivity; i.e. the catalysts simultaneously promote the reaction between the epoxy reactant and the phenolic hydroxyl group (or acid group) on the reactant and the aliphatic hydroxyl group(s) on the product giving branched or cross-linked polymers rather than the desired linear polymers. In still other instances, the reaction rate is unsatisfactory and/or the product is highly colored and thereafter unsatisfactory for many uses and/or the product was contaminated with corrosive anions (e.g. chloride) and is therefore unacceptable for electrical encapsulation (potting).

These and other problems have now been solved by the subject invention.

SUMMARY OF THE INVENTION

It has now been discovered that the trisubstituted (2,5-dihydroxyphenyl)phosphonium hydroxide inner salts, and the hydrolyzed derivatives thereof, are novel latent catalysts for promoting the reaction between vicinal epoxides and phenols and/or carboxylic acids (or anhydrides).

The novel catalysts are surprisingly effective in selectively catalyzing the desired reaction between the reactants at a suitable reaction rate. The reaction products are obtained in high yields and are of generally excellent color.

Additionally, the novel catalysts are surprisingly unreactive with epoxy resins at conventional storage temperatures. As a result, precatalyzed epoxy resins can now be produced by merely blending the subject catalysts with the epoxy resins. Such precatalyzed epoxy resins are, of course, novel compositions of matter.

The Novel Catalysts

The trisubstituted (2,5dihydroxyphenyl)phosphonium hydroxide inner salts correspond to formula I below

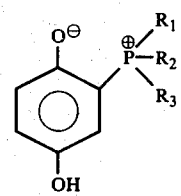

wherein $R_1$–$R_3$ are hydrocarbyl or inertly-substituted hydrocarbyl radicals, each of which independently has from 1 to about 20 carbon atoms. $R_1$, $R_2$, and $R_3$ are preferably each n-butyl or phenyl and are most preferably n-butyl.

The hydrolyzed derivatives of formula I correspond to formula II

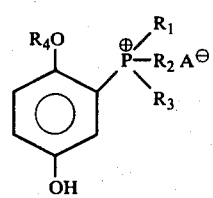

wherein $R_1$–$R_3$ have the aforesaid values; $R_4$ is hydrogen, benzyl or lower alkyl (1 to 6 carbon atoms); and $A^\ominus$ is a compatible neutralizing anion (such as chloride, bromide, iodide, bisulfate, chlorosulfonate, acetate, diacetate, trifluoromethylsulfonate, trifluoroacetate, adipate, acrylate, chloroacetate, trichloroacetate, etc.). The non-nucleophilic anions (such as bisulfate, acetate, diacetate, adipate, etc.) are preferred anions for precatalyzed resins. Bromide and iodide anions are the preferred nucleophilic anions. In formula II, $R_1$–$R_3$ are likewise preferably each n-butyl or phenyl and are most preferably n-butyl. $R_4$ is preferably hydrogen.

Compounds of formula I are prepared by reacting 1,4-benzoquinone with a tertiary phosphine measuring the change in torque of a constant speed agitator which is in contact with the polymer containing solution which change in torque is a function of a change in solution viscosity.

24. The process of claim 13 wherein the predetermined molecular weight is a weight average molecular weight which may vary from about 41,000 to about 127,000.

25. The process of claim 24 wherein the solution viscosity limits which correspond to said molecular weights may vary from about 5 to about 1000 poise.

26. A process for preparing a halogenated aromatic polyester having a predetermined molecular weight and of the recurring structural formula:

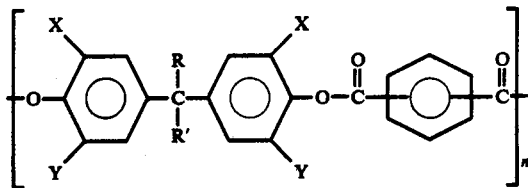

where X which may be the same or different is chlorine or bromine, Y which may be the same or different is hydrogen, chlorine or bromine, R and R' may be the same or different and represent lower alkyl groups, hydrogen, or together constitute a cyclic hydrocarbon group, and n equals at least 10, by the solution polymerization of a halogenated aromatic bisphenol and a diacid halide selected from the group consisting of isophthaloyl chloride, terephthaloyl chloride and mixtures thereof which comprises:

(I) providing a solution comprising:
  (a) an organic solvent
  (b) a halogenated aromatic bisphenol, and
  (c) an acid acceptor;
(II) adding an amount of said diacid halide to the solution of I, said amount being less than the amount necessary to achieve stoichiometric equivalence with the halogenated aromatic bisphenol, under conditions sufficient to react said diacid halide with the halogenated aromatic bisphenol of I to form a polymer;
(III) sensing the viscosity of the solution;
(IV) adding an additional amount of diacid halide in response to the sensed solution viscosity as the sensed solution viscosity approaches a predetermined solution viscosity limit; and
(V) terminating the addition of the diacid halide in response to the sensing of the predetermined solution viscosity limit.

27. The process of claim 26 wherein said halogenated aromatic polyester of the recurring structural formula is a product of tetrabromobisphenol A and a mixture of about 45 to 75% by weight isophthaloyl chloride and correspondingly about 55 to about 25% by weight terephthaloyl chloride.

28. The process of claim 26 wherein said halogenated aromatic polyester of the recurring structural formula is a product of tetrabromobisphenol A and a mixture of about 60% by weight isophthaloyl chloride and correspondingly about 40% by weight terephthaloyl chloride.

29. The process of claim 26 wherein said halogenated aromatic polyester of the recurring structural formula is a product of a tetrachlorobisphenol A and a mixture of about 90 to 40% by weight isophthaloyl chloride and correspondingly about 10 to 60% by weight terephthaloyl chloride.

30. The process of claim 26 wherein said halogenated aromatic polyester of the recurring structural formula is a product of tetrachlorobisphenol A and a mixture of about 70% by weight isophthaloyl chloride and correspondingly about 30% by weight terephthaloyl chloride.

31. The process of claim 26 wherein the acid acceptor is a tertiary amine.

32. The process of claim 26 wherein the solution polymerization is carried out at a temperature of about 15° to about 50° C.

33. The process of claim 26 wherein the solution polymerization is carried out at a pressure of about 0.1 to about 10 atmospheres.

34. The process of claim 26 wherein the organic solvent is selected from the group consisting of methylene chloride chloroform, tetrachloroethane, trichloroethane, chlorobenzene, chlorotoluene, dichloroethane, benzene, toluene, xylene and mixtures thereof.

35. The process of claim 26 wherein the viscosity of the resulting polymer containing solution is sensed by measuring the change in torque of a constant speed agitator which is in contact with the polymer containing solution which change in torque is a function of a change in solution viscosity.

36. The process of claim 26 wherein the predetermined molecular weight is a weight average molecular weight which may vary from about 50,000 to about 97,000.

37. The process of claim 36 wherein the solution viscosity limits which correspond to said molecular weights may vary from about 30 to about 95 poise.

* * * * *

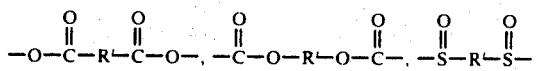

and —SO$_2$—R'—SO$_2$— radicals wherein R' is a bivalent hydrocarbon radical. 4,4'-Isopropylidenediphenol (i.e. bisphenol A) is the most preferred phenol).

The Carboxylic Acid Reactants

The organic carboxylic acids and anhydrides are likewise well known. The acids bear one or more carboxyl groups on the organic nucleus. The anhydrides are prepared from such carboxylic acids by the removal of water therefrom in an intra- or intermolecular condensation. This class of compounds therefore includes acetic, propionic, octanoic, stearic, acrylic, methacrylic, oleic, benzoic, phthalic, isophthalic, maleic, succinic, adipic, itaconic, polyacrylic and polymethacrylic acids, and the like, and anhydrides thereof, such as acetic anhydride, phthalic anhydride, hexahydrophthalic anhydride, etc.

There are two subclasses of carboxylic acids and anhydrides that are particularly important based on their reaction with epoxy resins.

The reaction of ethylenically unsaturated monocarboxylic acids with epoxy resins produces hydroxy-substituted esters or polyesters which are particularly useful in the preparation of coatings, adhesives, etc. See, for example, U.S. Pat. No. 3,377,406. Acrylic and methacrylic acid are particularly useful in this regard. Accordingly, the ethylenically unsaturated monocarboxylic acids are a preferred subclass of acids.

The second preferred subclass of acids is comprised of members which are useful in cross-linking epoxy resins. The members of this subclass are normally di- or tribasic acids, or anhydrides thereof, and are preferably liquid or low-melting solids, such as succinic, maleic or hexahydrophthalic acids or anhydrides and the like. Other such acids and anhydrides are shown, for example, in U.S. Pat. No. 2,970,983 and U.S. Pat. No. 3,547,885.

Ratio of Reactants

The ratio of vicinal epoxide reactant to phenol and/or carboxylic acid reactant in the subject process can vary over a wide range depending upon the product desired. E.g. if a product terminated with a phenolic ether group is desired, obviously one would employ an excess of phenol in the process, etc.

Solvents

In many instances the reactants are liquid and no solvent or diluent is needed. In other cases, however, where one or both of the reactants are solid or viscous liquids, an inert solvent or diluent can be used advantageously. Suitable such inert solvents or diluents are known to those skilled in the art and include ketones (such as acetone, methyl ethyl ketone, etc.), hydrocarbons (such as benzene, toluene, xylene, cyclohexane, ligroin, etc.) and the like.

Other Process Parameters

Generally, the reaction mixture is warmed at temperatures in the range of from about 50° C. to about 225° C. (preferably 100°-175° C.) until an exotherm begins and, after the exotherm has peaked, substantially warmed in the same range for an additional time to assure substantially complete reaction. Atmospheric or superatmospheric pressure (e.g. up to about 200 psig) are common.

The Reaction Products

The products here produced are generally known compounds in industry. The particular product produced will vary in properties depending upon the selection and ratio of reactants used in the process. Every combination of reactants of course need not be discussed but the following discussion will illustrate the types of products which can be produced.

The reaction products here produced by reacting an epoxy resin with a phenol in the presence of the subject catalysts are phenolic ethers bearing one or more aliphatic secondary hydroxyl groups. Such aliphatic hydroxyl groups are formed in the ring-opening reaction between the oxirane and phenolic hydroxyl groups. Additionally, the reaction products bear a terminal epoxy group(s) or a phenolic hydroxyl group(s) depending upon the ratio of reactants. Consequently, they are reactive intermediates which can be cured (crosslinked) with many polyfunctional curing agents to form hard, insoluble solid which are useful coatings. A list of several known curing agents which are suitable for use herein is found in U.S. Pat. No. 3,477,990. The cured products (particularly those of high molecular weight) are useful as surface coatings, as adhesive layers in laminates, coatings on filament windings, in structural binding applications, and the like. The reaction products prepared from halogenated (particularly brominated) phenols are particularly useful in flameproofing applications since they tend to be self-extinguishing. Thus, they are useful in forming cured coatings for wood paneling and as adhesive layers in wood laminates, etc.

The reaction products here produced by reacting an epoxy resin with a monocarboxylic acid (or anhydride of such acids) have terminal ester groups and are useful in coatings, adhesives, reinforced plastics, moldings, etc. The reaction products formed by reacting epoxy resins with polycarboxylic acids, or anhydrides thereof, are cross-linked insoluble resins used in coatings, etc.

Functional monomers are here produced by reacting a $C_2$ to $C_4$ alkylene oxide with acrylic or methacrylic acid. Hydraulic fluids are here prepared by reacting lower alkylene oxide with a phenol in substantially equimolar amounts. Nonionic surfactants are here prepared by reacting an alkylated monohydric phenol with a $C_2$ to $C_4$ alkylene oxide, or mixture of such alkylene oxides.

Other useful products can be similarly prepared by the reaction of vicinal epoxides with phenols and/or carboxylic acids (or anhydrides) in the presence of the subject catalysts.

The following examples further illustrate the invention:

EXPERIMENTS 1-7

This series of experiments was conducted by charging to a reaction vessel (equipped with a thermometer and mechanical stirrer and prepurged with nitrogen) a diglycidyl ether of bisphenol A having an epoxy equivalent weight of 187 (4.5 g.), bisphenol A (2.628 g.) and 0.011 g. of the phosphonium catalyst dissolved in methanol. The reaction mixture was warmed up to about 150° C. after which the heat was turned off. An exotherm was observed in each instance and after the exotherm subsided, the reaction mixture was heated at 160° C. for an additional 3 hours. The results of the experiments are shown in Table 1. All of the resins produced were of excellent color.

TABLE I
Epoxy Catalyst Screening Results to Prepare Linear High Molecular Weight Epoxy Resins

| Experiment No. | Catalyst | Theoretical Percent Epoxide | Actual % Epoxide Remaining |
|---|---|---|---|
| 1 | cyclohexane with ⊖O, ⊕P—(C₆H₅)₃, and OH substituents | 2.00 | 2.04 |
| 2 | cyclohexane with ⊖O, ⊕P—(n-C₄H₉)₃, and OH substituents | 2.00 | 2.00 |
| 3 | cyclohexane with OC₂H₅, ⊕P—(C₆H₅)₃ I⊖, and OH substituents | 2.00 | 2.05 |
| 4 | cyclohexane with OH, ⊕P—(C₆H₅)₃ HSO₄⊖, and OH substituents | 2.00 | 2.94 |
| 5 | cyclohexane with OH, ⊕P—C₆H₅)₃ ⊖O—C(=O)—CH₃, and OH substituents | 2.00 | 2.04 |
| 6 | cyclohexane with OH, ⊕P—(C₆H₅)₃ ⊖O₃S CH₃, and OH substituents | 2.00 | 2.85 |
| 7 | cyclohexane with OH, ⊕P—(C₆H₅)₃ Br⊖, and OH substituents | 2.00 | 2.20 |

EXPERIMENTS 8–14

This series of experiments was conducted in an analogous fashion except that here we used 2.812 g. of bisphenol A in each instance and the reaction mixtures were heated at 160° C. for 5 hours instead of the 3 hours used above. The results are summarized in Table II.

TABLE II
Epoxy Catalyst Screening Results to Prepare Linear High Molecular Weight Epoxy Resins

| Experiment No. | Catalyst | Theoretical Percent Epoxide | Actual % Epoxide Remaining |
|---|---|---|---|
| 8 | cyclohexane with ⊖O, ⊕P—(C₆H₅)₃, and OH substituents | 1.00 | 1.21 |
| 9 | cyclohexane with ⊖O, ⊕P-cn-C(n-C₄H₉)₃, and OH substituents | 1.00 | 1.11 |
| 10 | cyclohexane with OC₂H₅, ⊕P—(C₆H₅)₃ I⊖, and OH substituents | 1.00 | 1.26 |
| 11 | cyclohexane with OH, ⊕P—(C₆H₅)₃ HSO₄⊖, and OH substituents | 1.00 | 2.47 |
| 12 | cyclohexane with OH, ⊕P—C₆H₅)₃ ⊖O—C(=O)—CH₃, and OH substituents | 1.00 | 1.20 |
| 13 | cyclohexane with OH, ⊕P—(C₆H₅)₃ ⊖O₃S—C₆H₄—CH₃, and OH substituents | 1.00 | 2.37 |
| 14 | cyclohexane with OH, ⊕P—(C₆H₅)₃ Br⊖, and OH substituents | 1.00 | 1.36 |

EXPERIMENTS 15–31

This series of experiments was conducted in analogous fashion except that here we used 1.698 g. of bisphenol A in each instance and the reaction mixtures were heated at 160° C. for only 1.5 hours instead of the times used heretofore. The results are summarized in Table III.

TABLE III
Epoxy Catalyst Screening Results to Prepare Linear High Molecular Weight Epoxy Resins

| Experiment No. | Catalyst | Theoretical % Epoxide | Actual % Epoxide Remaining |
|---|---|---|---|
| 15 | cyclohexane with ⊖O, ⊕P—(n-C₄H₉)₃, and OH substituents | 8.00 | 7.90 |
| 16 | cyclohexane with OC₂H₅, ⊕P—(C₆H₅)₃ I⊖, and OH substituents | 8.20 | 8.28 |

TABLE III-continued
Epoxy Catalyst Screening Results to Prepare Linear High Molecular Weight Epoxy Resins

| Experiment No. | Catalyst | Theoretical % Epoxide | Actual % Epoxide Remaining |
|---|---|---|---|
| 17 | 1,4-dihydroxycyclohexyl-P⊕(C₆H₅)₃ Cl⊖ | 8.20 | 8.31 |
| 18 | 4-hydroxycyclohexyl-P⊕(nC₄H₉)₃ CF₃CO₂⊖ (with HO) | 8.00 | 7.65 |
| 19 | 4-hydroxycyclohexyl-P⊕(n-C₄H₉)₃ ClCH₂CO₂⊖ (with HO) | 8.00 | 7.95 |
| 20 | 4-hydroxycyclohexyl-P⊕(n-C₄H₉)₃ CH₂=CH—CO₂⊖ (with HO) | 8.00 | 8.09 |
| 21 | 4-hydroxycyclohexyl-P⊕(n-C₄H₉)₃ ⊖O₂C—(CH₂)₄—CO₂H (with HO) | 8.00 | 8.29 |
| 22 | 4-hydroxycyclohexyl-P⊕(C₆H₅)₃ CF₃CO₂⊖ (with HO) | 8.00 | 7.94 |
| 23 | 4-hydroxycyclohexyl-P⊕(C₆H₅)₃ NO₃⊖ (with HO) | 8.00 | 8.58 |
| 24 | 4-hydroxycyclohexyl-P⊕(C₆H₅)₃ CH₂=CH—CO₂⊖ (with HO) | 8.00 | 8.27 |
| 25 | 4-hydroxycyclohexyl-P⊕(C₆H₅)₃ ClCH₂CO₂⊖ (with HO) | 8.00 | 8.21 |
| 26 | 4-hydroxycyclohexyl-P⊕(C₆H₅)₃ Cl₃CCO₂⊖ (with HO) | 8.00 | 8.06 |
| 27 | 4-oxidocyclohexyl-P⊕[(CH₂)₇CH₃]₃ (with HO) | 8.00 | 7.94 |
| 28 | 4-oxidocyclohexyl-P⊕(CH₂—CH₂—CN)₃ (with HO) | 8.00 | 8.07 |
| 29 | 4-hydroxycyclohexyl-P⊕[(CH₂)₂CH₃]₃ ⊖O—C(=O)—CF₃ (with HO) | 8.00 | 7.62 |
| 30 | 4-hydroxycyclohexyl-P⊕(CH₂CH₂CN)₃ ⊖O—C(=O)—CF₃ (with HO) | 8.00 | 7.65 |
| 31 | 2-oxido-4-hydroxycyclohexyl-P⊕(CH₂OH)₃ | 8.00 | 10.75 |

Experiments 1–31 demonstrate that the instant catalysts are particularly good latent catalysts for promoting the reaction between epoxy resins and phenols.

EXPERIMENTS 18–23

In this series of experiments an epoxy resin having an epoxy equivalent weight of 172–178 (100.0 g.) and hexahydrophthalic anhydride (80.0 g.) and the instant catalyst (0.15 g.) were thoroughly mixed and maintained under a vacuum for at least 15 minutes or until bubbling under vacuum was very slight. The reaction mixture was then warmed at 110° C. for 2 hours, the heat turned off and the exotherm allowed to subside. The reaction mixture was then heated at 150° C. for an additional 2 hours (12 hours for Experiment 18) and cooled. In every instance, the cured product was clear, colorless and very hard. The catalysts are described in Table VI.

TABLE IV
Catalyst Screening Results to Cross-Link Epoxy Resins with Anhydrides

| Experiment No. | Catalyst |
|---|---|
| 32 | 1,3-dihydroxy-(OH,OH)cyclohexyl-P⊕(C₆H₅)₃ HSO₄⊖ |
| 33 | 1,3-dihydroxycyclohexyl-P⊕(C₆H₅)₃ ⊖O—C(=O)—CH₃ |
| 34 | ethoxy-hydroxycyclohexyl-P⊕(C₆H₅)₃ I⊖ |

TABLE IV-continued
Catalyst Screening Results to Cross-Link
Epoxy Resins with Anhydrides

| Experiment No. | Catalyst |
|---|---|
| 35 | 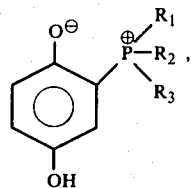 |
| 36 | 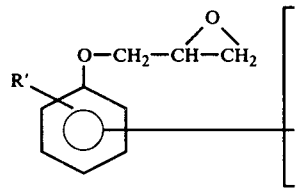 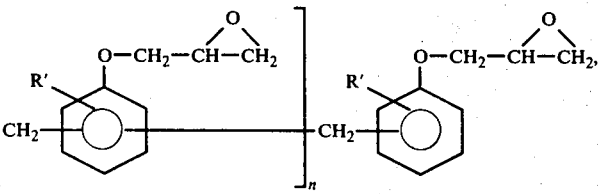 |
| 37 | 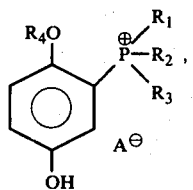 |

In a companion series of experiments, aliquots of the above mixtures were maintained for two weeks at room temperature prior to curing and no appreciable change in the viscosity of the uncured mixtures was noted.

Similar good results were noted in another series of experiments wherein the hexahydrophthalic anhydride used in the above formulations was replaced with dodecenylsuccinic and nadic methyl anhydrides but longer cure schedules were required.

Experiments 32-37 demonstrate that the instant catalysts are particularly effective as latent catalyst in promoting the reaction between epoxy resins and anhydrides.

Similarly, the instant catalyst would be useful in promoting the reaction between epoxy resins and blends of phenols and carboxylic acids and/or anhydrides.

The cured products from Experiments 1-37 strongly adhered to the reaction vessel and were useful as protective coatings.

Other species of the instant catalyst can be similarly used. In addition, modifications of the above experiments can be made. For example, the above anhydrides can be replaced with other anhydrides such as maleic anhydride leading to cross-linked products. Alternatively, acrylic or methacrylic acid could be used in the reaction conditions leading to epoxy resins terminated with a free-radical or thermally polymerizable vinyl groups. Such compounds are likewise useful as coating materials.

Other such variations of the instant invention will be readily apparent to one of ordinary skill in the art.

We claim:

1. A precatalyzed epoxy resin composition comprising (a) an epoxy resin bearing an average of more than one vicinal epoxy group per molecule and (b) a small but catalytic amount of a trisubstituted (2,5-dihydroxyphenyl)phosphonium hydroxide inner salt corresponding to formula I $$\text{(formula I)}$$

wherein $R_1$–$R_3$ are hydrocarbyl or inertly-substituted hydrocarbyl radicals, each of which independently has from 1 to about 20 carbon atoms; or a hydrolyzed derivative of I corresponding to formula II $$\text{(formula II)}$$

wherein $R_1$–$R_3$ have the aforesaid values, $R_4$ is hydrogen, benzyl or lower alkyl, and $A^\ominus$ is a compatible neutralizing anion.

2. The composition defined by claim 1 wherein the catalyst corresponds to formula I.

3. The composition defined by claim 1 in which the catalyst corresponds to formula II.

4. The composition defined by claim 1 in which $R_1$, $R_2$, and $R_3$ are each n-butyl or phenyl.

5. The composition defined by claim 4 in which $R_1$, $R_2$, and $R_3$ are n-butyl.

6. The composition defined by claim 4 in which $A^\ominus$ is bromide, iodide, or a non-nucleophilic anion.

7. The composition defined by claim 5 in which the catalyst corresponds to formula I.

8. The composition defined by claim 5 in which the catalyst corresponds to formula II in which $A^\ominus$ is bromide, iodide, or a non-nucleophilic anion.

9. The composition defined by claim 8 wherein said non-nucleophilic anion is bisulfate, acetate, diacetate, chloroacetate, trifluoroacetate, acrylate, or adipate.

10. The composition defined by claim 9 wherein $A^\ominus$ is chloroacetate and $R_4$ is hydrogen.

11. The composition defined by claim 1 which additionally comprises (c) a phenol, (b) being present in an amount sufficient to catalyze the reaction between (a) and (c) when the reaction mixture is warmed at a temperature of from about 50° to about 225° C.

12. The composition defined by claim 11 wherein (a) is an epoxy resin corresponding to the formula wherein R' is hydrogen or alkyl and n is from about 0.1 to about 10; or said polyepoxide corresponds to the formula

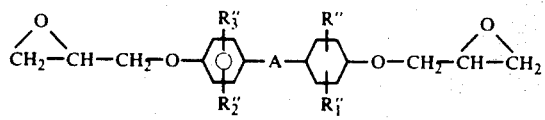

wherein R″, R″₁, R″₂ and R″₃ are each independently hydrogen, chlorine or bromine and A is alkylene or akylidene of from 1 to 4 carbon atoms or A is

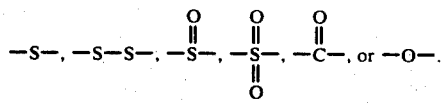

13. The composition defined by claim 12 wherein n is from about 1 to about 2 and wherein A is alkylene or akylidene.

14. The composition defined by claim 11 wherein $R_1$, $R_2$ and $R_3$ are each n-butyl or phenyl, and $A^\ominus$ is bromide, iodide, or a non-nucleophilic anion.

15. The composition defined by claim 14 wherein
(a) is the diglycidyl ether of bisphenol A.
(b) corresponds to formula I, and
(c) is bisphenol A.

16. The composition defined by claim 14 wherein
(a) is the diglycidyl ether of bisphenol A,
(b) corresponds to formula II, and
(c) is bisphenol A.

17. The composition defined by claim 16 wherein said non-nucleophilic anion is bisulfate, acetate, diacetate, chloroacetate, trifluoroacetate, acrylate or adipate.

18. The composition defined by claim 17 wherein $R_1$, $R_2$ and $R_3$ are each n-butyl and $A^\ominus$ is chloroacetate and $R_4$ is hydrogen.

19. The composition defined by claim 11 wherein (c) is bisphenol A.

20. In the process of reacting an epoxy compound bearing one or more vicinal epoxy groups per molecule with a phenol to thereby form a β-hydroxyalkyl ether of said phenol, the improvement comprising conducting said process in the presence of a small but catalytic amount of a trisubstituted (2,5-dihydroxyphenyl)phosphonium hydroxide inner salt corresponding to formula I

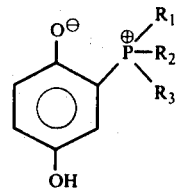

wherein $R_1$-$R_3$ are hydrocarbyl or inertly-substituted hydrocarbyl radicals, each of which independently has from 1 to about 20 carbon atoms; or a hydrolyzed derivative of I corresponding to formula II wherein $R_1$-$R_3$ have the aforesaid values, $R_4$ is hydrogen, benzyl or lower alkyl, and $A^\ominus$ is a compatible neutralizing anion.

21. The process defined by claim 20 wherein said epoxy compound is an epoxy resin bearing an average of more than one vicinal epoxy group per molecule.

22. The process defined by claim 21 wherein said phenol is bisphenol A.

23. The process defined by claim 20 wherein said epoxy compound is a vicinal alkylene oxide of from 2 to about 24 carbon atoms.

24. The process defined by claim 23 wherein said epoxy compound is ethylene oxide, propylene oxide, 1,2-butylene oxide or epichlorohydrin.

25. The process defined by claim 24 wherein said phenol is bisphenol A.